(12) United States Patent
Kawamura et al.

(10) Patent No.: US 7,304,192 B2
(45) Date of Patent: Dec. 4, 2007

(54) METHOD FOR PRODUCING CHLORINATED HYDROCARBON HAVING CHLORINATED TERTIARY CARBON

(75) Inventors: Takeshi Kawamura, Takasago (JP); Chiho Yoshimi, Takasago (JP); Hidetoshi Odaka, Takasago (JP)

(73) Assignee: Kaneka Corporation, Osaka (JP)

( * ) Notice: Subject to any disclaimer, the term of this patent is extended or adjusted under 35 U.S.C. 154(b) by 426 days.

(21) Appl. No.: 10/520,538

(22) PCT Filed: Jul. 2, 2003

(86) PCT No.: PCT/JP03/08453

§ 371 (c)(1),
(2), (4) Date: Jan. 7, 2005

(87) PCT Pub. No.: WO2004/009520

PCT Pub. Date: Jan. 29, 2004

(65) Prior Publication Data

US 2005/0250968 A1    Nov. 10, 2005

(30) Foreign Application Priority Data

Jul. 18, 2002  (JP) .............................. 2002-209041
Aug. 19, 2002  (JP) .............................. 2002-237853

(51) Int. Cl.
*C07C 17/16*    (2006.01)

(52) U.S. Cl. .................. 570/258; 570/190; 570/191; 570/194; 570/216

(58) Field of Classification Search ................ 570/194, 570/191, 190, 216, 258
See application file for complete search history.

(56) References Cited

FOREIGN PATENT DOCUMENTS

| JP | 10 175892 | 6/1998 |
|----|-----------|--------|
| JP | 11 302205 | 11/1999 |

OTHER PUBLICATIONS

Supplementary European Search Report No. 03 74 1172, dated May 24, 2006.

*Primary Examiner*—Elvis O. Price
(74) *Attorney, Agent, or Firm*—Kenyon & Kenyon LLP

(57) ABSTRACT

The present invention relates to a simple method for efficiently producing aromatic-substituted chlorinated hydrocarbons, for example, high-purity cumyl chloride (1,4-bis(1-chloro-1-methylethyl)benzene, p-DCC) that can be used as an initiator for cationic polymerization. A corresponding tertiary alcohol such as 1,4-bis(1-hydroxy-1-methylethyl)benzene is mixed with aqueous hydrochloric acid and subjected to stirring, and then the resulting organic layer is brought into contact with a hydrogen chloride gas to produce high-quality aromatic-substituted chlorinated hydrocarbon in high yield. Furthermore, in order to purify a mixture containing a chlorinated hydrocarbon compound, the mixture being produced by reaction between an aqueous solution of a metal hypochlorite and a protonic acid, the mixture is allowed to react with an aqueous alkaline solution to form an alcohol compound. Then, a solid is isolated by solid-liquid separation and chlorinated again with the aqueous hydrochloric acid. As a result, a high-purity chlorinated hydrocarbon compound is produced in high yield.

17 Claims, No Drawings

METHOD FOR PRODUCING CHLORINATED HYDROCARBON HAVING CHLORINATED TERTIARY CARBON

This is a 371 national phase application of PCT/JP2003/008453 filed 2 Jul. 2003, claiming priority to Japanese Application Nos. 2002-209041 filed 18 Jul. 2002, and 2002-237853 filed 19 Aug. 2002, the contents of which are incorporated herein by reference.

TECHNICAL FIELD

The present invention provides a novel and simple method for efficiently producing chlorinated hydrocarbons from aromatic-substituted alcohol compounds. The present invention also relates to a method for producing a chlorinated hydrocarbon by selectively chlorinating a tertiary carbon in a hydrocarbon compound with a hypochlorite compound. Such chlorinated hydrocarbons produced according to the present invention are useful as reagents for various synthetic reactions due to their reactive chlorine-substituted groups. It is known that aromatic-substituted chlorinated hydrocarbons, such as 1,4-bis(1-chloro-1-methylethyl)benzene [1,4-dicumyl chloride, p-Cl(CH$_3$)$_2$CC$_6$H$_4$C(CH$_3$)$_2$Cl], are used as cationic polymerization initiators in producing polyisobutylene having terminal functional groups or block copolymers each containing a block component composed of polyisobutylene, for example, styrene-isobutylene-styrene copolymers [U.S. Pat. Nos. 4,276,394 and 5,527,870 (Maeda et al. 1994)].

BACKGROUND ART

The following processes for producing such initiators from 1,4-diisopropylbenzene are known.

In one process, 1,4-diisopropenylbenzene (CH$_2$=(CH$_3$)CC$_6$H$_4$C(CH$_3$)=CH$_2$) is prepared by dehydrogenation (U.S. Pat. No. 3,429,941) and then undergoes addition reaction with hydrogen chloride (O. Nuyken et al., Makromol. Chem., 186, 173 (1985)). In another process, 1,4-bis(1-hydroxy-1-methylethyl)benzene (1,4-HO(CH$_3$)$_2$CC$_6$H$_4$C(CH$_3$)$_2$OH) is prepared by air oxidation (for example, Japanese Unexamined Patent Application Publication No. 60-174737) and is then allowed to react with hydrogen chloride (V. S. C. Chang et al., Polymer Bulletin, 4, 513 (1981)).

The above-described processes require at least two-step operations. A process for producing target 1,4-dicumylchloride in a single-step operation by allowing 1,4-diisopropylbenzene (1,4-H(CH$_3$)$_2$CC$_6$H$_4$C(CH$_3$)$_2$H) to react with a chlorine gas under sunlight irradiation is disclosed (M. S. Kharashch et al., J. Am. Chem. Soc., 61, 2142 (1939)). A reaction induced by light irradiation has a problem with the control of regioselectivity in chlorination.

However, each of such conventional processes uses a hydrogen chloride gas or a chlorine gas functioning as a reagent for chlorination, thus leading to gas-liquid reaction when the processes are performed. Therefore, there are problems in which yield is significantly affected by reaction conditions, such as stirring efficiency, and a large excess of a chlorinating reagent is required based on stoichiometry. Furthermore, the reaction must be performed at ice temperature. Consequently, these processes are not industrially advantageous processes.

The present inventors found a process for simply producing dicumyl chloride or the like in high yield by allowing an alcohol compound, such as 1,4-bis(1-hydroxy-1-methylethyl)benzene 1,4-HO(CH$_3$)$_2$CC$_6$H$_4$C(CH$_3$)$_2$OH, to react with hydrochloric acid (Japanese Unexamined Patent Application Publication Nos. 8-291090 and 10-175892).

With respect to a process for producing 1,4-dicumyl chloride by chlorination of the benzylic positions in 1,4-diisopropylbenzene, a process in which sodium hypochlorite is allowed to react in the presence of a phase-transfer catalyst (BU$_4$N(HSO$_4$)) is disclosed (H. E. Fonouni et al., J. Am. Chem. Soc, 1983, 105, 7672). However, this process uses an expensive phase-transfer catalyst and thus is not an industrially advantageous. A process in which chlorination is performed with hypochlorous acid without a phase-transfer catalyst is also disclosed (F. Minisci et al., Chim. Ind., 70, 52 (1988). A process for producing 1,4-dicumyl chloride by chlorination of tertiary carbons in 1,4-diisopropylbenzene with hypochlorous acid has the advantages of being a single step and higher selectivity compared with photochlorination. However, hypochlorous acid is a significantly unstable substance; hence, it is difficult to constantly prepare hypochlorous acid of the same concentration and store the prepared hypochlorous acid. Therefore, when a specific amount of feed is set based on an amount of a material, the equivalent relation between them does not stay the same, thus resulting in difficulties in achieving stable yield, stable selectivity, and stable product quality.

A process for producing 1,4-dicumyl chloride with hypochlorous acid is also disclosed in Japanese Unexamined Patent Application Publication No. 9-143106 but does not solve the above-described problems. Thus, Japanese Unexamined Patent Application Publication No. 9-143106 does not provide a production process suitable for commercialization. Japanese Unexamined Patent Application Publication No. 2000-63303 also discloses a process for producing 1,4-dicumyl chloride with hypochlorous acid. A crystallization operation is necessary for achieving higher purity and is performed using a refrigerator with the high expense of electricity. This results in an inevitable reduction in yield.

DISCLOSURE OF INVENTION

It is an object of the present invention to provide an easier method for producing a high-quality chlorinated hydrocarbon compound, such as dicumyl chloride, that can be used as an initiator for cationic polymerization.

Furthermore, even when a chlorination reaction is efficiently performed with a hypochlorous acid compound, introducing chlorine into only a desired position with high selectivity has a limitation. A subsequent purifying operation, such as crystallization, reduces yield. This results in the difficulties with achieving commercially stable yield, stable selectivity, and stable product quality.

The present inventors found that chlorination performed by allowing aromatic group-substituted alcohol to react with aqueous hydrochloric acid functioning as a chlorinating reagent provides a high-quality chloride in high yield without subsequent crystallization or drying of an organic layer containing the product. This finding has led to the completion of the present invention. In a method for producing a chlorinated hydrocarbon compound with hypochlorous acid, it is another object to increase purity and yield. The present inventors elucidated the problems in detail and conducted extensive studies on a method for solving the problems. As a result, the present inventors found a method for increasing the purity of a target compound by hydrolyzing the reaction products under an alkaline condition to form an alcohol compound, which is a selectively isolated solid. This also has led to the completion of the present invention.

The present invention relates to method (A) for producing a chlorinated hydrocarbon compound represented by general formula (2):

$$C_nR^1{}_mH_k(CR^2R^3Cl)_j \qquad (2)$$

(where n is an integer of 1 to 12; m and k each represent an integer of 0 to 25; j is an integer of 1 to 10; $R^1$ represents an atom selected from the group consisting of chlorine, bromine, iodine, oxygen, nitrogen, sulfur, and phosphorus, and $R^1$ may be the same or different when m is 2 or more; a j-valent group represented by $C_nR^1{}_mH_k$ has no tertiary carbon-hydrogen bond; and $R^2$ and $R^3$ each represent a saturated aliphatic hydrocarbon group containing 1 to 5 carbon atoms or a saturated aliphatic hydrocarbon group containing 1 to 5 carbon atoms having hydrogen atoms partially substituted with halogen atoms, and $R^2$ and $R^3$ have no tertiary carbon-hydrogen bond) by allowing a compound represented by general formula (1):

$$C_nR^1{}_mH_k(CR^2R^3OH)_j \qquad (1)$$

(where m, n, k, j, $R^1$, $R^2$, and $R^3$ are the same as above) to react in the presence of aqueous hydrochloric acid and separating an organic layer by oil-water separation and then bringing the resulting organic layer into contact with a hydrogen chloride gas;

method (B) for producing a chlorinated hydrocarbon compound represented by general formula (2) by mixing a mixture containing the chlorinated hydrocarbon compound represented by general formula (2) with an aqueous alkaline solution, the mixture being produced by reaction between an aqueous solution of a metal hypochlorite, a protonic acid, and a compound represented by general formula (3):

$$C_nR^1{}_mH_k(CHR^2R^3)_j \qquad (3)$$

(where m, n, k, j, $R^1$, $R^2$, and $R^3$ are the same as above), for purification to prepare a compound represented by general formula (1) and then allowing the resulting reaction product (solid), which is preferably isolated by solid-liquid separation, to react in the presence of aqueous hydrochloric acid; and method (C) for producing a chlorinated hydrocarbon compound represented by general formula (2) by allowing the reaction product (solid) prepared in method (B) to react in the presence of aqueous hydrochloric acid and separating an organic layer by oil-water separation and then bringing the resulting organic layer into contact with a hydrogen chloride gas.

According to a preferred embodiment, the production method is characterized in that the compound represented by general formula (1) is an aromatic hydrocarbon containing a 1-hydroxy-1-methylethyl substituent.

According to another preferred embodiment, the production method is characterized in that the metal hypochlorite is selected from the group consisting of potassium hypochlorite, sodium hypochlorite, calcium hypochlorite, barium hypochlorite, copper hypochlorite, and copper(II) hypochlorite.

According to another preferred embodiment, the production method is characterized in that the protonic acid is selected from the group consisting of hydrochloric acid, sulfuric acid, and acetic acid.

According to another preferred embodiment, the production method is characterized in that the aqueous alkaline solution is an aqueous solution of sodium hydroxide or an aqueous solution of potassium hydroxide.

According to another preferred embodiment, the production method is characterized in that a halogenated organic solvent is used when the compound represented by general formula (2) is produced from the compound represented by general formula (3).

According to another preferred embodiment, the production method is characterized in that the halogenated organic solvent is used when the compound represented by general formula (2) is produced from the compound represented by general formula (3), the halogenated organic solvent being selected from the group consisting of monochlorobenzene, dichlorobenzene, trichlorobenzene, ethyl chloride, ethylene dichloride, carbon tetrachloride, chloroform, methylene chloride, 1-trichloro-2-trifluoroethane, and trifluoromethylbenzene.

According to another preferred embodiment, the production method is characterized in that an aromatic hydrocarbon solvent or an aliphatic hydrocarbon solvent is used in the step of mixing the aqueous alkaline solution to produce the compound represented by general formula (1) and then performing solid-liquid separation, and each of the solvents is also used for washing the resulting solid.

According to another preferred embodiment, the production method is characterized in that the aromatic hydrocarbon solvent or the aliphatic hydrocarbon solvent is used in the step of mixing the aqueous alkaline solution to produce the compound represented by general formula (1) and then performing solid-liquid separation, the solvents each being selected from the group consisting of pentane, cyclopentane, hexane, cyclohexane, heptane, benzene, toluene, and xylene.

According to another preferred embodiment, the production method is characterized in that a saturated hydrocarbon solvent, an aromatic hydrocarbon solvent, or a halogenated organic solvent is used when the compound represented by general formula (2) is produced from the compound represented by general formula (1).

According to another preferred embodiment, the production method is characterized in that the saturated hydrocarbon solvent, the aromatic hydrocarbon solvent, or the halogenated organic solvent used to produce the compound represented by general formula (2) from the compound represented by general formula (1) is selected from the group consisting of pentane, cyclopentane, neopentane, hexane, cyclohexane, heptane, methylcyclohexane, octane, norbornene, ethylcyclohexane, benzene, toluene, xylene, ethylbenzene, butyl chloride, and ethyl chloride.

Examples of the aromatic-substituted alcohol represented by general formula (1) include (1-hydroxy-1-methylethyl)benzene $C_6H_5C(CH_3)_2OH$, 1,4-bis(1-hydroxy-1-methylethyl)benzene 1,4-HO$(CH_3)_2CC_6H_4C(CH_3)_2$OH, 1,3-bis(1-hydroxy-1-methylethyl)benzene 1,3-HO$(CH_3)_2CC_6H_4C(CH_3)_2$OH, 1,3,5-tris(1-hydroxy-1-methylethyl)benzene 1,3,5-((C$(CH_3)_2$OH)$_3C_6H_3$,and 1,3-bis(1-hydroxy-1-methylethyl)-5-(tert-butyl)benzene 1,3-((HOC$(CH_3)_2$)2-5-(C$(CH_3)_3)C_6H_3$.

A hydrocarbon compound represented by general formula (3)

$$C_nR^1{}_mH_k(CHR^2R^3)_j \qquad (3)$$

(where n is an integer of 1 to 12; m and k each represent an integer of 0 to 25; j is an integer of 1 to 10; $R^1$ represents an atom selected from the group consisting of chlorine, bromine, iodine, oxygen, nitrogen, sulfur, and phosphorus, and $R^1$ may be the same or different when m is 2 or more; a j-valent group represented by $C_nR^1{}_mH_k$ has no tertiary carbon-hydrogen bond; and $R^2$ and $R^3$ each represent a saturated aliphatic hydrocarbon group containing 1 to 5 carbon atoms or a saturated aliphatic hydrocarbon group containing 1 to 5 carbon atoms having hydrogen atoms partially substituted with halogen atoms, and $R^2$ and $R^3$ have no tertiary carbon-hydrogen bond) can be used as a material for the present invention. $R^2$ and $R^3$ shown in the formula preferably each represent a hydrocarbon group such as a methyl group, an ethyl group, or an n-propyl group; or a hydrocarbon group containing a substituent, such as a chlorine atom, on a carbon atom in the hydrocarbon group. In particular, $R^2$ and $R^3$ each preferably represent a methyl group to form an isopropyl group.

Furthermore, a compound represented by general formula (4):

$$C_6H_{6-z}(CHR^4R^5)_z \qquad (4)$$

(where z is an integer of 1 to 4; and $R^4$ and $R^5$ each represent a saturated aliphatic hydrocarbon group containing 1 to 5 carbon atoms and has no tertiary carbon-hydrogen bond) can be suitably used. $R^4$ and $R^5$ preferably each include a hydrocarbon group such as a methyl group, an ethyl group, and n-propyl group. In particular, $R^4$ and $R^5$ each preferably represent a methyl group to form an isopropyl group.

Preferable examples of a compound represented by general formula (3) of the present invention include the following:

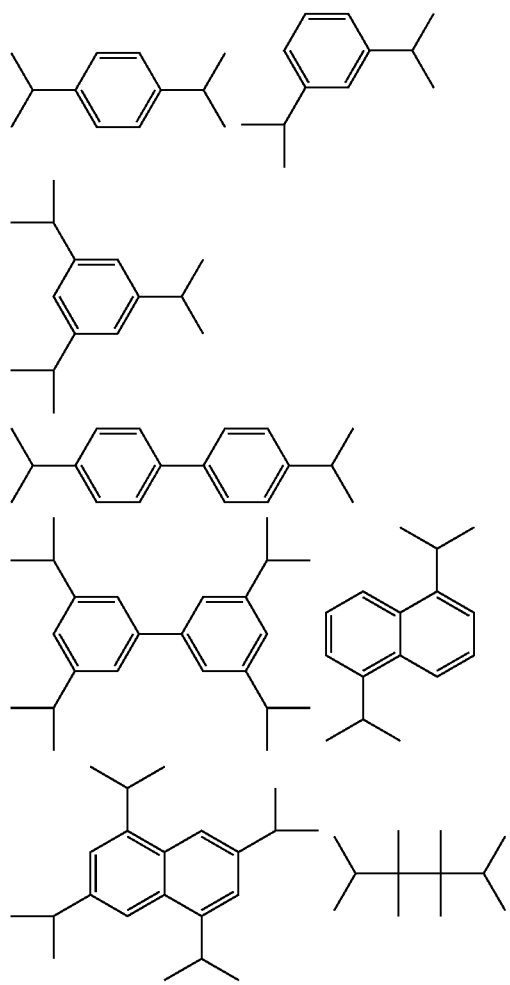

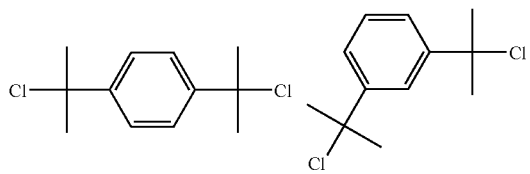

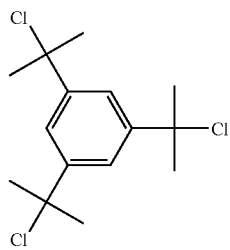

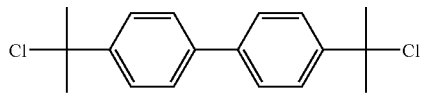

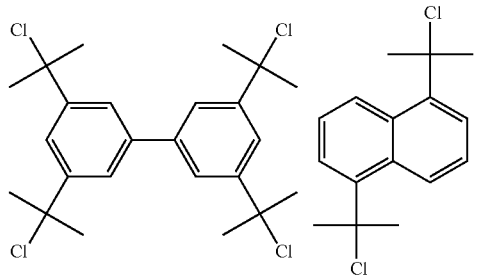

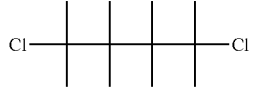

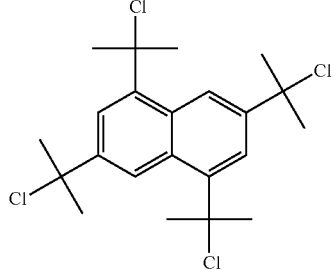

The present invention provides a chlorinated hydrocarbon compound represented by general formula (2):

$$C_nR^1{}_mH_k(CR^2R^3Cl)_j \qquad (2)$$

(where m, n, k, j, $R^1$, $R^2$, and $R^3$ are the same as above) is provided by the present invention. Preferable examples of the compound include the following:

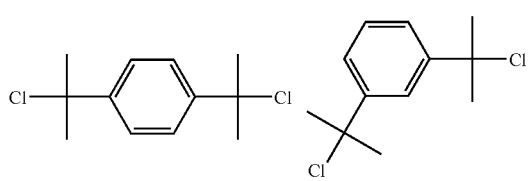

-continued

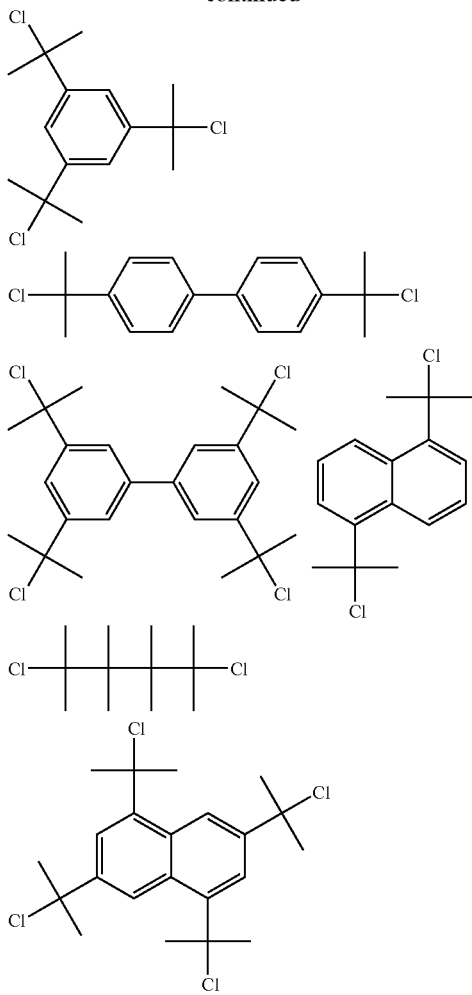

In the present invention, usually, to a mixture containing an organic solvent and an alcohol compound represented by general formula (1) is added aqueous hydrochloric acid, followed by stirring to produce a chlorinated hydrocarbon compound. The order of addition may be changed according to need, for example, the limitation of the production. The resulting target compound is dissolved in an organic solvent. As a result, the organic layer containing the target compound and an aqueous layer of aqueous hydrochloric acid are present. Since only the organic layer is required, the aqueous layer of hydrochloric acid is separated from the organic layer. At this point in time, the target compound has not always satisfactory purity. In particular, the alcohol compound undergoes dehydration, which is a side reaction in the reaction with aqueous hydrochloric acid, to form an olefin containing, for example, an isopropenyl group, thereby reducing the purity. In order to achieve higher purity, a hydrogen chloride gas is brought into contact with the organic layer. Contact with the hydrogen chloride gas causes not only chlorination of the unreacted alcohol that remains when reaction with aqueous hydrochloric acid is insufficient, but also addition reaction between the hydrogen chloride gas and the olefin containing an isopropenyl group or the like, which is a by-product, to form a target compound, thus resulting in higher purity. The hydrogen chloride gas may be brought into contact with the organic layer by, but not particularly limited to, a common technique employed for gas-liquid reaction, such as a technique for bubbling a hydrogen chloride gas or a technique for mixing in a stirring vessel pressurized by a hydrogen chloride gas.

Examples of the organic solvent used in the present reaction include, but are not particularly limited insofar as a known solvent is used, saturated hydrocarbons such as pentane, cyclopentane, neopentane, hexane, cyclohexane, heptane, methylcyclohexane, octane, norbornene, and ethylcyclohexane; aromatic hydrocarbons such as benzene, toluene, xylene, and ethylbenzene; halogenated hydrocarbons such as carbon tetrachloride, chloroform, methylene chloride, chloroethane, dichloroethane, propyl chloride, butyl chloride, and ethyl chloride; ketones such as acetone, methyl ethyl ketone, and diethyl ketone; ethers such as diethyl ether, diisopropyl ether, dibutyl ether, and dimethoxyethane; alcohols such as methanol, ethanol, isopropanol, and butanol; and dimethylformamide, dimethyl sulfoxide, and HMPA.

Among these, saturated hydrocarbons, aromatic hydrocarbons, and halogenated organic solvents are preferable because of low solubility for hydrochloric acid and ease of industrial use. Pentane, cyclopentane, neopentane, hexane, cyclohexane, heptane, methylcyclohexane, octane, norbornene, ethylcyclohexane, benzene, toluene, xylene, ethylbenzene, butyl chloride, and ethyl chloride are more preferable.

In the present invention, usually, the temperature during the reaction with aqueous hydrochloric acid and a hydrogen chloride gas is preferably set at $-10°$ C. to $40°$ C., and more preferably $0°$ C. to $30°$ C., from the standpoints of reaction rate and stability of a target substance.

The amount of the solvent used in the reaction is preferably, but is not particularly limited to, 1 to 100 times, and more preferably 3 to 10 times, that of the alcohol in weight ratio, from the standpoint of subsequent handling.

The hydrogen chloride content of aqueous hydrochloric acid used in the present invention is not particularly limited insofar as the hydrogen chloride content is one equivalent or more based on the hydroxyl group content, but is preferably two equivalents or more based on the hydroxyl group content in order to efficiently produce the target compound.

A hydrogen chloride gas introduced into a reactor is difficult to react completely as long as at least a vapor phase is present in the reactor. After introducing the gas into the reactor, the gas is dissolved and/or dispersed in the solution and then consumed by reaction. The amount of the hydrogen chloride gas used in the present invention is not particularly limited insofar as the amount of the gas consumed is one equivalent or more based on the amount of an impurity containing, for example, an isopropenyl group. In order to efficiently achieve higher purity, the amount of the gas consumed is more preferably two equivalents or more based on the amount of the impurity. In order to increase the reaction rate and/or to reduce the amount of the remaining impurity by increasing the amount of the hydrogen chloride gas dissolved in the solution, increasing the partial pressure of the hydrogen chloride gas in the vapor phase is effective.

After the reaction, the hydrogen chloride gas remaining in the solution containing a target substance is degassed by a common degassing process, for example, a process for reducing pressure or bubbling an inert gas through the solution.

According to the chlorination method of the present invention with aqueous hydrochloric acid and subsequently with the hydrogen chloride gas, a higher reaction temperature can be set compared with the reaction temperature in a reaction system using a hydrogen chloride gas alone disclosed in the above-described literature (Polymer Bulletin, 4, 513-520 (1981)) In the reaction system using the hydrogen chloride gas alone, the reaction must be performed at a temperature of approximately 0° C. According to the method of the present invention, a side reaction is suppressed even at about room temperature, and a target compound can be produced in high yield. That is, in this method, the reaction can be performed at a temperature of 10° C. or higher. In order to increase the reaction rate, the reaction temperature can be set at 15° C. to 30° C., furthermore, at 20° C. to 30° C. An increase in reaction temperature eliminates the need for cooling and thus simplifies the production facility, thereby reducing production costs.

Examples of the metal hypochlorite used in the present invention include, but are not limited to, potassium hypochlorite, sodium hypochlorite, calcium hypochlorite, barium hypochlorite, copper hypochlorite, and copper(II) hypochlorite. Among these, sodium hypochlorite is preferable from the standpoints of ease of industrial use, ease of handling, and excellent yield and selectivity. The concentration of the aqueous solution containing the metal hypochlorite is not particularly limited but is preferably 0.7 mol/kg or higher from the standpoints of excellent yield and selectivity. When an aqueous solution of sodium hypochlorite obtained has a concentration of 0.7 mol/kg or higher, the solution may be diluted with water for use. In this case, the water means, for example, tap water, ion-exchanged water, or distilled water, and may contain a metal salt, for example, NaCl or KCl, in some cases.

The amount of the aqueous solution containing the metal hypochlorite is not particularly limited insofar as the chlorine content is one equivalent or more based on the theoretical amount. A largely excess amount of the aqueous solution containing the metal hypochlorite used causes the side reaction to proceed and thus may result in the target compound with low purity. Accordingly, in order to efficiently produce the target compound with high purity, the molar chlorine content is preferably 1.0 to 10 times, and particularly preferably 1.0 to 5 times, based on the theoretical amount.

Examples of the protonic acid used in the present invention include, but are not particularly limited, hydrochloric acid, sulfuric acid, nitric acid, and acetic acid. Among these, hydrochloric acid is preferable from the standpoints of excellent yield and selectivity. With respect to a process for adding the protonic acid, a continuous addition or a stepwise addition is preferable, but a single-step addition may be employed. For the continuous addition, the addition time is preferably 0.5 to 15 minutes, and particularly preferably 1 to 5 minutes. The protonic acid should be used in an amount such that the pH of the aqueous layer in the reaction system is preferably adjusted in the range of 4 to 9, more preferably 5 to 7. The concentration of the protonic acid used is not particularly limited but is preferably relatively higher concentration from the standpoints of, for example, quality, reaction time, and the capacity of a reaction vessel for production on an industrial scale. Concentrated hydrochloric acid containing at least 35 percent by weight hydrogen chloride is particularly preferable.

In the present invention, the chlorination reaction from a compound represented by general formula (3) to a compound represented by general formula (2) may be performed without solvent but is preferably performed in a state in which materials are diluted with an organic solvent. The organic solvent is not particularly limited but is preferably a halogenated organic solvent, which is not easily degraded by chlorination and thus has potential for maintaining the effect of addition. Preferably used are monochlorobenzene, dichlorobenzene, trichlorobenzene, ethyl chloride, ethylene dichloride, carbon tetrachloride, chloroform, methylene chloride, 1-trichloro-2-trifluoroethane, and trifluoromethylbenzene. Monochlorobenzene, dichlorobenzene, trifluoromethylbenzene, and ethyl chloride are particularly preferably used.

The temperature during the chlorination reaction is not particularly limited, but the reaction is preferably performed at a low temperature because hypochlorous acid is relatively unstable. The reaction is preferably performed at a temperature of −15° C. to 40° C., and more preferably −5° C. to 25° C. Reaction temperatures of higher than 40° C. accelerate the decomposition of hypochlorous acid. As a result, the concentration of hypochlorous acid is reduced to substantially zero in the middle of the reaction. Reaction temperatures of lower than −15° C. are not preferable due to ease of freezing. Hypochlorous acid is decomposed to generate a hazardous chlorine gas; consequently, the reaction is preferably performed at the above-described temperature range from the standpoint of safety.

After the chlorination reaction, the resulting mixture containing a chlorinated hydrocarbon compound represented by general formula (2) contains a large number of impurities, for example, by-products formed by the chlorination reaction. Thus, the target chlorinated hydrocarbon has low purity. In order to efficiently remove the impurities, for example, by-products, the mixture is mixed with an aqueous alkaline solution to form a compound represented by general formula (1):

$$C_n R^1_m H_k (CR^2 R^3 OH)_j \quad (1)$$

(where m, n, k, j, $R^1$, $R^2$, and $R^3$ are the same as above), and then the resulting compound is isolated as a solid by solid-liquid separation, followed by purification.

The aqueous alkaline solution used in the present invention is not particularly limited but is preferably an aqueous solution of a metal hydroxide. An aqueous solution of sodium hydroxide or an aqueous solution of potassium hydroxide is particularly preferable due to ease of handling and ease of availability. Sodium hydroxide or potassium hydroxide may be used in the form of a solid as it is.

The alcoholization with the aqueous alkaline solution may be performed without a solvent or with the remaining organic solvent used in the previous reaction as is, but is preferably performed in a state in which an organic solvent is further added to dilute the materials. The organic solvent is not particularly limited but is preferably aromatic hydrocarbon or aliphatic hydrocarbon, from the standpoints of high reaction selectivity; and, in the step of performing solid-liquid separation and then purification by washing with an organic solvent, low solubility for an target alcohol compound represented by general formula (1) and high solubility for impurities. Among these, preferably used are pentane, cyclopentane, hexane, cyclohexane, heptane, benzene, toluene, and xylene, and particularly preferably hexane. The organic solvent is preferably added in an amount of 10 to 200 parts by weight, and particularly preferably 50 to 100 parts by weight, based on the amount of the organic layer containing the organic solvent used in the previous reaction.

The temperature during the alcoholization reaction with an aqueous alkaline solution is not particularly limited, but the reaction is preferably performed at a temperature of 40° C. to 100° C., and particularly preferably 50° C. to 80° C., from the standpoints of reaction rate and reaction selectivity. Lower reaction temperatures require a prolonged period of time for ensuring yield of a target compound represented by general formula (1). On the contrary, higher reaction temperatures are not preferable from the standpoint of the effect of an aqueous alkaline solution in the reaction vessel on the material of the reaction vessel.

With respect to the alkali content of an aqueous alkaline solution used in the present invention, when, for example, an aqueous solution of sodium hydroxide or an aqueous solution of potassium hydroxide is used, the alkali content is preferably 0.1 to 10 percent by weight, more preferably 1 to 5 percent by weight. Lower contents require a large amount of the solution and are thus not preferable from the standpoint of the capacity of the reaction vessel. Higher contents are not preferable from the standpoints of the effect on the material of the reaction vessel and a decrease in reaction selectivity. The reaction vessel is preferably a glass-lined vessel or a Teflon-lined vessel for avoiding deterioration of quality.

Instead of feeding a large amount of the aqueous alkaline solution in a single operation, the solution may be added in twice or more. This avoids adding an aqueous alkali solution with a high concentration at a time but is able to add at least an equivalent amount of an aqueous alkali solution with a low concentration required.

In solid-liquid separation for an alcohol compound represented by general formula (1), a common solid-liquid separation process, such as centrifugal separation or pressure filtration with a filter cloth, can be performed. In order to reduce the amount of a liquid as an impurity adhering to a solid, for example, increasing a centrifugal force, prolonging filtration time, and removing the liquid by the passage of a gas such as nitrogen are effective. Furthermore, performing solid-liquid separation and then adding an organic solvent and/or pure water are repeated. This procedure is effective in order to reduce impurities adhering to the solid. The organic solvent added preferably has low solubility for an alcohol compound represented by general formula (1). Aromatic hydrocarbons and aliphatic hydrocarbons, which are the organic solvents used for the alcoholization described above, may be used. Toluene and hexane are particularly preferable. During the addition of such an organic solvent, if possible, stirring or mixing of the solution is also effective.

As described above, to the solid alcohol compound represented by general formula (1) that is subjected to solid-liquid separation and then purified is added aqueous hydrochloric acid to yield a chlorinated hydrocarbon compound, which is a target compound of the present invention, represented by general formula (2) with high purity. This process may be performed by the same process as that described above.

The resulting chlorinated hydrocarbon compound, which is represented by general formula (2), produced by this reaction has high purity and thus can be used as it is. If higher purity is required, subsequently, the resulting aqueous layer of hydrochloric acid is separated by oil-water separation, and then a hydrogen chloride gas is introduced into the vapor phase or the liquid phase of the organic layer containing the target compound, thereby being brought into contact with the organic layer. As a result, higher purity is achieved.

Chlorinated hydrocarbon compounds, which are represented by general formula (2), produced according to the present invention are used as reagents for various synthetic reactions due to their reactive chlorine-substituted groups. In particular, the present invention provides chlorinated hydrocarbon compounds with high purity. Thus, the compounds are suitably used as initiators for the production of polyisobutylene with controlled terminal functional groups or various block copolymers each containing a block composed of polyisobutylene, for example, styrene-isobutylene-styrene copolymers.

BEST MODE FOR CARRYING OUT THE INVENTION

The present invention will now be described in detail based on examples. However, the present invention is not limited to these.

EXAMPLE 1

To a conical beaker were fed 0.14 kg of toluene and 0.03 kg of 1,4-bis(1-hydroxy-1-methylethyl)benzene (p-DIOL, manufactured by MITSUI PETROCHEMICAL Co., LTD.) and then added 0.25 kg of 35 wt % aqueous hydrochloric acid. This resulting mixture was stirred with a magnetic stirrer for 90 minutes at 20° C. At this time, both of organic and aqueous layers changed to transparent and colorless. After the organic layer was separated from the aqueous layer, a hydrogen chloride gas was bubbled through the organic layer for 90 minutes at 20° C. under stirring with the magnetic stirrer. Then, in order to remove hydrogen chloride, a nitrogen gas was bubbled for 45 minutes. A sample solution of the resulting toluene solution of ,1,4-bis(1-chloro-1-methylethyl)benzene (p-DCC) was devolatilized by distillation. The subsequent measurement of a 1H-NMR spectrum of the resulting p-DCC (crude) showed a purity of 99.5%. The resulting solution of p-DCC had high quality comparable to p-DCC produced by crystallization from an organic layer instead of contact with hydrogen chloride gas and drying, and was able to be satisfactorily used as an initiator for cationic polymerization.

EXAMPLE 2

The target compound was produced as in EXAMPLE 1 except that 35 wt % aqueous hydrochloric acid was used in an amount of 0.125 kg and the contact reaction with the hydrogen chloride gas was performed at 5° C. As a result, p-DCC with 99.5% purity determined by NMR was produced. The resulting solution of p-DCC had high quality comparable to p-DCC produced by crystallization from an organic layer and drying, and was able to be satisfactorily used as an initiator for cationic polymerization.

EXAMPLE 3

To a glass separable flask, having a capacity of 0.002 m$^3$, equipped with a thermometer, a baffle, and a stirrer were added 1,4-diisopropylbenzene (0.045 kg), monochlorobenzene (0.03 kg), and an aqueous solution of sodium hypochlorite (1.2 kg, 0.9 mol/kg) under stirring and cooling in an ice bath. Subsequently, concentrated aqueous hydrochloric acid (0.08 kg, 35 percent by weight) was slowly added dropwise to the solution through a dropping funnel over a period of 3 minutes and stirring was continued for 60 minutes. After the reaction, the organic layer and the aqueous layer was separated by standing. To the separated organic layer was added concentrated hydrochloric acid (0.03 kg, 35 percent by weight), and then the resulting mixture was vigorously stirred for about 5 minutes to deactivate the hypochlorous acid finely dispersed in the organic layer. The resulting organic layer was separated to obtain a monochlorobenzene solution of the reaction product. The yield of 1,4-bis(1-chloro-1-methylethyl)benzene in the product was determined by gas chromatography (hereinafter, referred to as "GC") analysis (yield: 60.0%).

To the same flask that was cleaned were added the separated monochlorobenzene solution, 0.04 kg of hexane, and 1 kg of an aqueous solution containing 2 wt % sodium hydroxide, and then stirring was continued for 5 hours at 60° C. The aqueous layer was alkaline through the reaction. This hydrolysis reaction provided 1,4-bis(1-hydroxy-1-methylethyl)benzene with a selectivity of about 90%.

Subsequently, the resulting solid was washed with hexane and pure water and then stirred in the presence of 0.3 kg of 35 wt % concentrated hydrochloric acid and 0.05 kg of toluene to yield 1,4-bis(1-chloro-1-methylethyl)benzene The purity determined by NMR was 95%. The ultimate yield was 45%.

EXAMPLE 4

The target compound was produced as in EXAMPLE 3 except that, in alcoholization, the reaction temperature was 50° C., and the reaction time was 8 hours. The alcoholization provided 1,4-bis(1-hydroxy-1-methylethyl)benzene with a selectivity of about 90%. The subsequent operation was performed as in EXAMPLE 3 to yield 1,4-bis(1-chloro-1-methylethyl)benzene at the end. The purity determined by NMR was 95%. The ultimate yield was 45%.

EXAMPLE 5

The target compound was produced as in EXAMPLE 3 except that the aqueous solution of 1 wt % sodium hydroxide was first added and the aqueous solution of 25 wt % sodium hydroxide was added in an amount of 0.04 kg after the confirmation that the aqueous layer showed acidic pH. The alcoholization provided 1,4-bis(1-hydroxy-1-methylethyl) benzene with a selectivity of about 90%. The subsequent operation was performed as in EXAMPLE 3 to yield 1,4-bis(1-chloro-1-methylethyl)benzene at the end. The purity determined by NMR was 95%. The ultimate yield was 45%.

EXAMPLE 6

The target compound was produced as in EXAMPLE 3 except that, instead of hexane, toluene was used as both the organic solvent added during alcoholization and the organic solvent for washing the formed solid and the reaction temperature was set at 75° C. The alcoholization provided 1,4-bis(1-hydroxy-1-methylethyl)benzene with a selectivity of about 70%.

The purity, which was determined by NMR, of 1,4-bis(1-chloro-1-methylethyl)benzene was 95%. The ultimate yield was 35%.

EXAMPLE 7

Subsequently to EXAMPLE 3, a hydrogen chloride gas was bubbled through the toluene solution of 1,4-bis(1-chloro-1-methylethyl)benzene which was the solution obtained at the end, under stirring with a magnetic stirrer for 1.5 hours at 25° C. As a result, 1,4-bis(1-chloro-1-methylethyl)benzene finally obtained had a purity of 99.5% determined by NMR. The ultimate yield was about 50%.

EXAMPLE 8

Subsequently to EXAMPLE 3, a hydrogen chloride gas was bubbled through the toluene solution of 1,4-bis(1-chloro-1-methylethyl)benzene which was the solution obtained at the end, for 1.5 hours at 5° C. As a result, 1,4-bis(1-chloro-1-methylethyl)benzene finally obtained had a purity of 99.0% determined by NMR. The ultimate yield was about 50%.

Comparative Example 1

With respect to the purity of p-DCC before the hydrogen chloride gas was introduced in EXAMPLE 1, a 1H-NMR spectrum was measured after volatile contents were distilled off. As a result, the purity was 98.0%.

Comparative Example 2

With respect to the purity of p-DCC before the hydrogen chloride gas was introduced in EXAMPLE 2, a 1H-NMR spectrum was measured after volatile contents were distilled off. As a result, the purity was 97.0%.

Comparative Example 3

In EXAMPLE 3, hexane was added alone instead of hexane and the aqueous solution of 2 wt % sodium hydroxide, followed by cooling crystallization. The purity of 1,4-bis(1-chloro-l-methylethyl)benzene in the dry crystals obtained was determined to be 90% by NMR. The ultimate yield was 30%.

INDUSTRIAL APPLICABILITY

According to the present invention, high-purity chlorinated hydrocarbon compounds represented by general formula: $C_nR^1{}_mH_k(CR^2R^3Cl)_j$ can be efficiently produced in high yield. The compounds are useful as reagents for various synthetic reactions due to their reactive chlorine-substituted groups.

The invention claimed is:

1. A method for producing a chlorinated hydrocarbon compound represented by general formula (2):

$$C_nR^1{}_mH_k(CR^2R^3Cl)_j \qquad (2)$$

(where n is an integer of 1 to 12; m and k each represent an integer of 0 to 25; j is an integer of 1 to 10; $R^1$ represents an atom selected from the group consisting of chlorine, bromine, iodine, oxygen, nitrogen, sulfur, and phosphorus, and $R^1$ may be the same or different when m is 2 or more; a j-valent group represented by $C_nR^1{}_mH_k$ has no tertiary carbon-hydrogen bond; and $R^2$ and $R^3$ each represent a saturated aliphatic hydrocarbon group containing 1 to 5 carbon atoms or a saturated aliphatic hydrocarbon group containing 1 to 5 carbon atoms having hydrogen atoms partially substituted with halogen atoms, and $R^2$ and $R^3$ have no tertiary carbon-hydrogen bond), the method comprising:

allowing a compound represented by general formula (1):

$$C_nR^1{}_mH_k(CR^2R^3OH)_j \qquad (1)$$

(where m, n, k, j, $R^1$, $R^2$, and $R^3$ are the same as above) to react in the presence of aqueous hydrochloric acid;

separating an organic layer by oil-water separation; and bringing the separated organic layer into contact with a hydrogen chloride gas.

2. The method for producing a chlorinated hydrocarbon compound according to claim 1, wherein the compound represented by general formula (2) is produced from the compound represented by general formula (1) in the presence of an organic solvent and aqueous hydrochloric acid.

3. The method for producing a chlorinated hydrocarbon compound according to claim 2, wherein the organic solvent for producing the chlorinated hydrocarbon compound represented by general formula (2) from the compound represented by general formula (1) is selected from the group consisting of a saturated hydrocarbon solvent, an aromatic hydrocarbon solvent and a halogenated organic solvent.

4. The method for producing a chlorinated hydrocarbon compound according to claim 3, wherein the organic solvent for producing the chlorinated hydrocarbon compound represented by general formula (2) from the compound represented by general formula (1) is at least one solvent selected from the group consisting of pentane, cyclopentane, neopentane, hexane, cyclohexane, heptane, methylcyclohexane, octane, norbornene, ethylcyclohexane, beuzene, toluene, xylene, ethylbenzene, butyl chloride, and ethyl chloride.

5. The method according to claim 2, wherein the compound represented by general formula (1) is an aromatic hydrocarbon containing a 1-hydroxy-1-methylethyl substituent.

6. The method for producing a chlorinated hydrocarbon compound according to claim 1, further comprising:
allowing a compound represented by general formula (3):

(where m, n, k, j, $R^1$, $R^2$, and $R^3$ are the same as above) to react with an aqueous solution of a metal hypochlorite and a protonic acid; and
mixing the reaction mixture with an aqueous alkaline solution to yield the compound represented by general formula (1).

7. A method for producing a chlorinated hydrocarbon compound represented by general formula (2) according to claim 1 comprising:
subjecting a mixture having a chlorinated hydrocarbon compound represented by general formula (2) to solid-liquid separation, the mixture being produced by reaction between an aqueous solution of a metal hypochlorite, a protonic acid, and a compound represented by general formula (3):

(where m, n, k, j, $R^1$, $R^2$, and $R^3$ are the same as above);
mixing the resulting solid material with an aqueous alkaline solution to form a compound represented by general formula (1); and
allowing the resulting compound to react in the presence of aqueous hydrochloric acid.

8. The method according to claim 7, wherein the metal hypochlorite is selected from the group consisting of potassium hypochlorite, sodium hypochlorite, calcium hypochlorite, barium hypochlorite, copper hypochlorite, and copper (II) hypochlorite.

9. The method according to claim 7, wherein the protonic acid is selected from the group consisting of hydrochloric acid, sulfuric acid, and acetic acid.

10. The method according to claim 6, wherein the aqueous alkaline solution is an aqueous solution of sodium hydroxide or potassium hydroxide.

11. The method according to claim 6, wherein a halogenated organic solvent is used for producing the compound represented by general formula (2) from the compound represented by general formula (3).

12. The method according to claim 11, wherein the halogenated organic solvent used for producing the compound represented by general formula (2) from the compound represented by general formula (3) is a halogenated organic solvent selected from the group consisting of monochlorobenzene, dichlorobenzene, trichlorobenzene, ethyl chloride, ethylene dichloride, carbon tetrachloride, chloroform, methylene chloride, 1-trichloro-2-trifluoroethane, and trifluoromethylbenzene.

13. The method according to claim 6, wherein an aromatic hydrocarbon or aliphatic hydrocarbon organic solvent is used in the step of mixing the aqueous alkaline solution to produce the compound represented by general formula (1) and then performing separation by filtration, and also used for washing the resulting solid.

14. The method according to claim 13, wherein the aromatic hydrocarbon or aliphatic hydrocarbon organic solvent used in the step of mixing the aqueous alkaline solution to produce the compound represented by general formula (1) and then performing separation by filtration is a solvent selected from the group consisting of pentane, cyclopentane, hexane, cyclohexane, heptane, benzene, toluene, and xylene.

15. The method for producing a chlorinated hydrocarbon compound according to claim 2, wherein the temperature during the reaction with the aqueous hydrochloric acid and the hydrogen chloride gas is 0° C. to 30° C.

16. The method for producing a chlorinated hydrocarbon compound according to claim 2, wherein the hydrogen chloride molar content is not less than two equivalents based on the hydroxyl group molar content.

17. The method for producing a chlorinated hydrocarbon compound according to claim 2, wherein an aromatic-substituted alcohol represented by general formula (1) is at least one member selected from 1,4-bis(1-hydroxy-1-methylethyl)benzene, 1,3-bis(1-hydroxy-1-methylethyl)benzene, and 1,3-bis(1-hydroxy-1-methylethyl)-5-(tert-butyl)benzene.

* * * * *

UNITED STATES PATENT AND TRADEMARK OFFICE
CERTIFICATE OF CORRECTION

PATENT NO.        : 7,304,192 B2                                             Page 1 of 1
APPLICATION NO.   : 10/520538
DATED             : December 4, 2007
INVENTOR(S)       : Kawamura et al.

It is certified that error appears in the above-identified patent and that said Letters Patent is hereby corrected as shown below:

Item [57] Abstract, line 14, "metal hypochiorite" should be changed to --metal hypochlorite--;

Column 12, line 30, "solution of ,1,4-bis(1-chloro-1-methylethyl)benzene" should be changed to --solution of 1,4-bis(1-chloro-1-methylethyl)benzene--;

Column 13, line 61, "EXAMPLE 3,a" should be changed to --EXAMPLE 3, a--;

Column 15, line 20 (claim 4, line 8), "norbomene" should be changed to --norborneme--;

Column 15, line 20 (claim 4, line 8), "beuzene" should be changed to --benzene--; and Column 15, lines 43-44 (claim 7, lines 7-8), "hypochiorite" should be changed to --hypochlorite--.

Signed and Sealed this

Tenth Day of March, 2009

JOHN DOLL
*Acting Director of the United States Patent and Trademark Office*